United States Patent [19]
Humphrey

[11] Patent Number: 5,607,401
[45] Date of Patent: Mar. 4, 1997

[54] AUGMENTED POLYMERIC HYPODERMIC DEVICES

[76] Inventor: Bruce H. Humphrey, P.O. Box 07513, Milwaukee, Wis. 53207

[21] Appl. No.: 402,974

[22] Filed: Mar. 10, 1995

Related U.S. Application Data

[63] Continuation of Ser. No. 120,657, Sep. 13, 1993, abandoned, which is a continuation-in-part of Ser. No. 754,457, Sep. 3, 1991, abandoned.

[51] Int. Cl.$^6$ ............................. A61M 5/00; A61M 5/31
[52] U.S. Cl. ...................... 604/239; 604/272; 606/182
[58] Field of Search ..................... 604/239, 272, 604/236, 264, 158, 256, 246, 273, 274, 232; 128/764, 770, 771; 606/181, 167, 182, 183

[56] References Cited

U.S. PATENT DOCUMENTS

| | | | |
|---|---|---|---|
| 1,147,408 | 7/1915 | Kells | 604/272 X |
| 2,512,568 | 6/1950 | Saffir | 604/239 |
| 2,512,569 | 6/1950 | Saffir | 604/272 |
| 2,524,713 | 10/1950 | Plechas | 604/272 X |
| 2,697,437 | 12/1954 | Everett | 604/273 X |
| 2,830,587 | 4/1958 | Everett | 604/272 |
| 2,904,045 | 9/1959 | Owings | 604/274 |
| 2,954,768 | 10/1960 | Hamilton | 604/274 |
| 2,989,053 | 6/1961 | Hamilton | 604/274 |
| 3,090,384 | 5/1963 | Baldwin et al. | 604/272 |
| 3,112,747 | 12/1963 | Cowley | 604/197 |
| 3,831,814 | 8/1974 | Butler | 222/81 |
| 3,884,230 | 5/1975 | Wulff | 604/273 X |
| 4,545,376 | 10/1985 | Beiter | 606/181 |
| 4,613,329 | 9/1986 | Bodicky | 604/158 |
| 4,737,146 | 4/1988 | Amaki et al. | 604/51 |
| 4,775,369 | 10/1988 | Schwartz | 604/263 |
| 4,795,446 | 1/1989 | Fecht | 604/264 |
| 4,838,877 | 6/1989 | Massau | 604/272 |
| 4,840,622 | 6/1989 | Hardy | 604/264 |
| 4,846,799 | 7/1989 | Tanaka et al. | 604/158 |
| 4,858,607 | 8/1989 | Jordan et al. | 604/182 |
| 4,889,117 | 12/1989 | Stevens | 606/181 |
| 4,929,237 | 5/1990 | Medway | 604/198 |
| 4,936,827 | 6/1990 | Grimm et al. | 604/60 |
| 4,957,488 | 9/1990 | Cameron et al. | 604/161 |
| 4,990,154 | 2/1991 | Brown et al. | 606/182 |
| 4,994,068 | 2/1991 | Hafnagle | 606/181 |
| 5,014,718 | 5/1991 | Mitchen | 128/771 |
| 5,071,411 | 12/1991 | Hillstead | 604/246 |
| 5,250,066 | 10/1993 | Lambert | 606/181 |
| 5,314,442 | 5/1994 | Morita | 606/182 |
| 5,344,611 | 9/1994 | Vogler et al. | 422/101 |
| 5,383,885 | 1/1995 | Bland | 606/182 |

FOREIGN PATENT DOCUMENTS

| | | | |
|---|---|---|---|
| 0017999 | 10/1980 | European Pat. Off. | 606/181 |
| 1039161 | 10/1953 | France | 604/272 |
| 2641963 | 7/1990 | France | 606/181 |
| 2164363 | 7/1973 | Germany | 604/239 |
| 3323867 | 1/1985 | Germany . | |
| 0160468 | 10/1982 | Japan | 604/272 |

*Primary Examiner*—Randall L. Green
*Assistant Examiner*—V. Alexander

[57] ABSTRACT

This invention relates to augmented polymeric hypodermic needles and lancets. The needles and lancets are stiffened by augmenting means so that they are able to pierce the skin. The devices cost less to manufacture and are safer to use than present metal hypodermic devices. They make possible new types of ampules, phlebotomy devices and intravenous catheters. Most of the models are completely burnable. This invention makes possible safe, easy to use, low cost, disposable hypodermic devices for injection, blood withdrawal and testing.

18 Claims, 11 Drawing Sheets

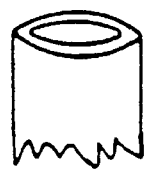
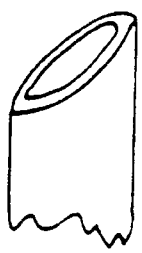
FIG.10  FIG.11  FIG.12
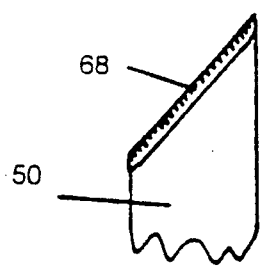
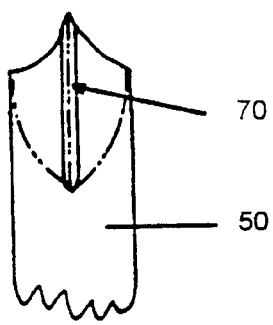
FIG.13  FIG.14
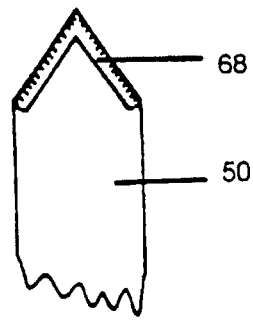
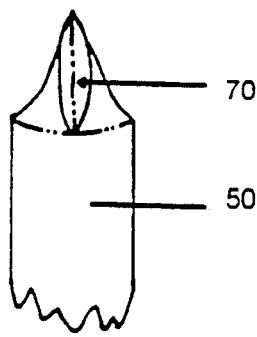
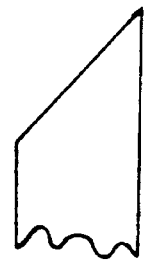
FIG.15  FIG.16  FIG.18
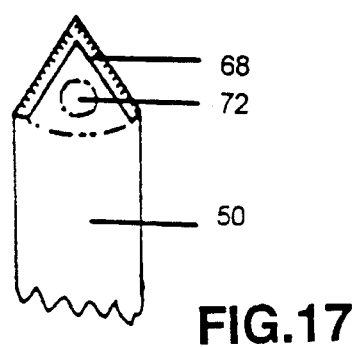
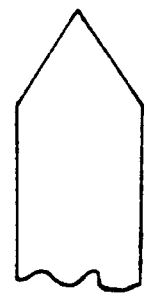
FIG.17  FIG.19

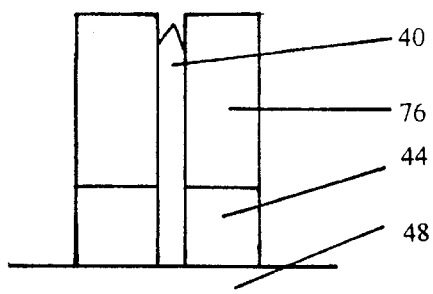
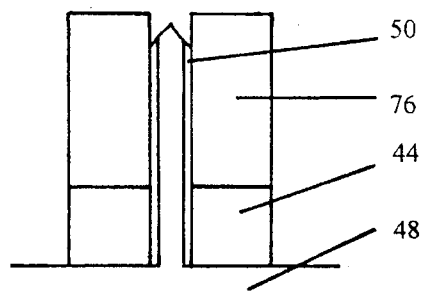
FIG. 28  FIG. 29
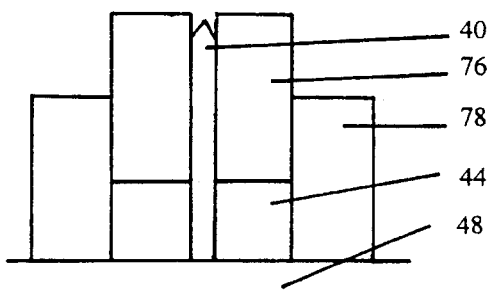
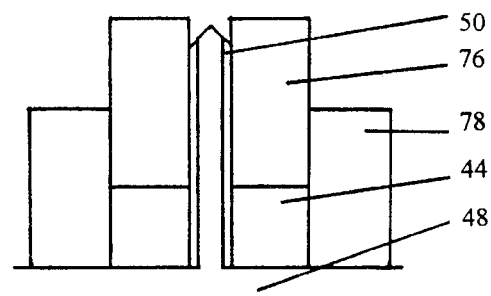
FIG. 30  FIG. 31
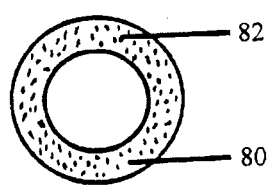
FIG. 32
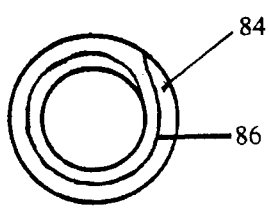
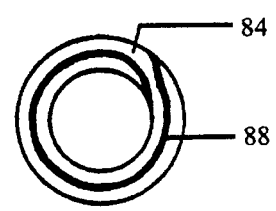
FIG. 33  FIG. 34

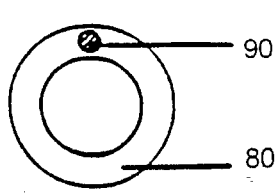
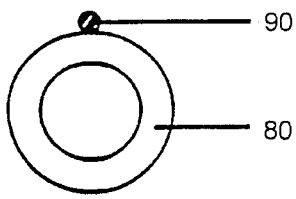
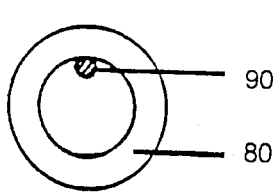
FIG. 35　　　　FIG. 36　　　　FIG. 37
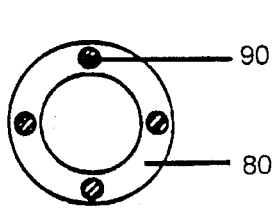
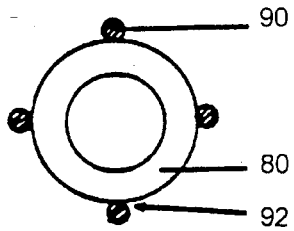
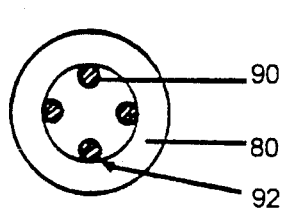
FIG. 38　　　　FIG. 39　　　　FIG. 40
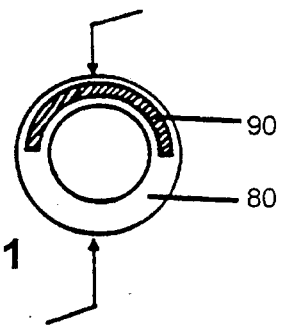
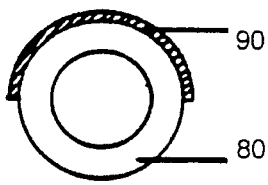
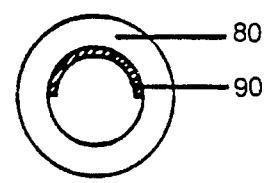
FIG. 41　　　　FIG. 42　　　　FIG. 43
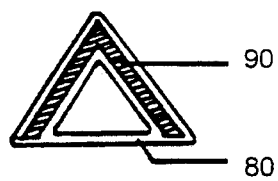
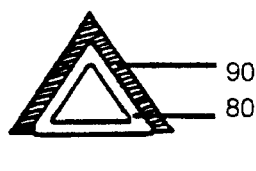
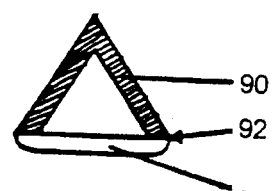
FIG. 44　　　　FIG. 45　　　　FIG. 46
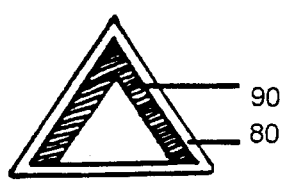
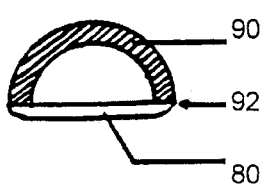
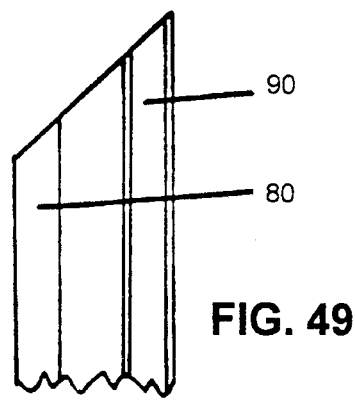
FIG. 47　　　　FIG. 48　　　　FIG. 49

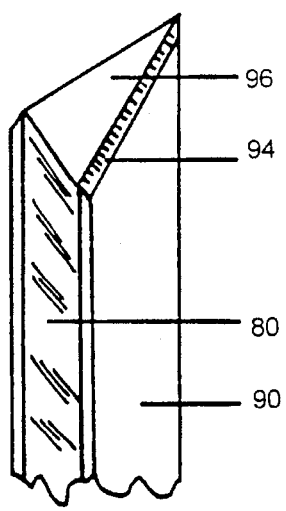
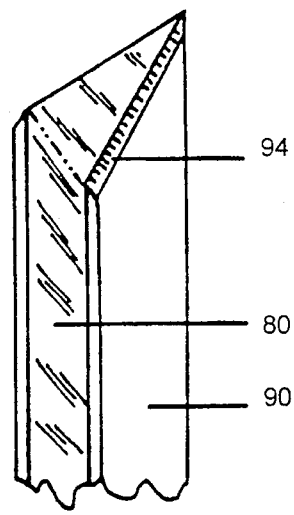
FIG. 50    FIG. 51
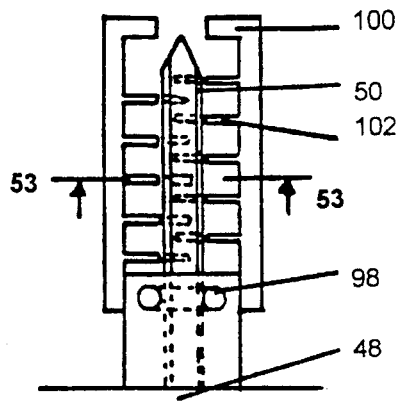
FIG. 52
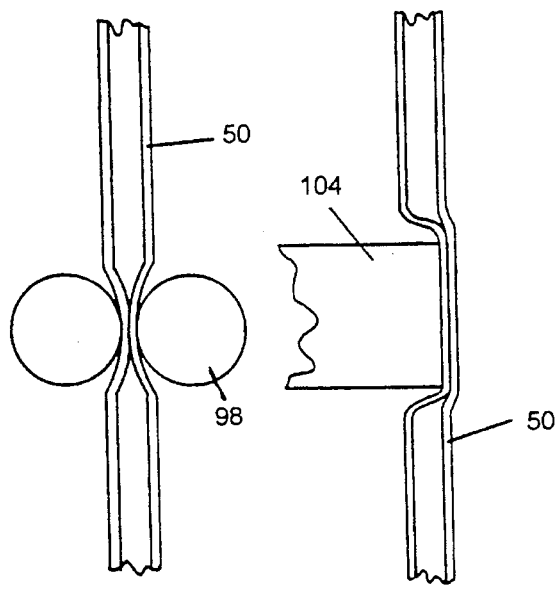
FIG. 54    FIG. 55
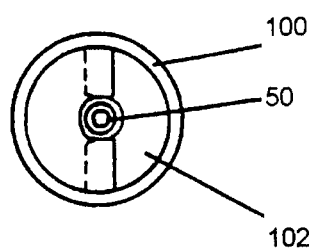
FIG. 53
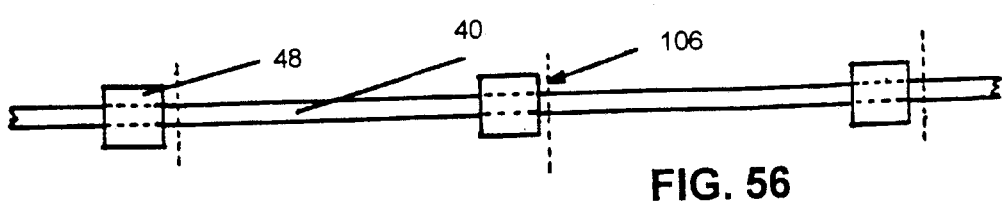
FIG. 56

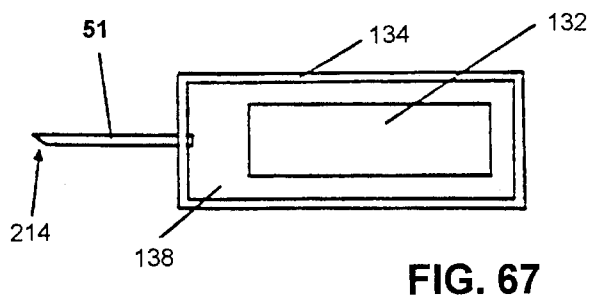
FIG. 67
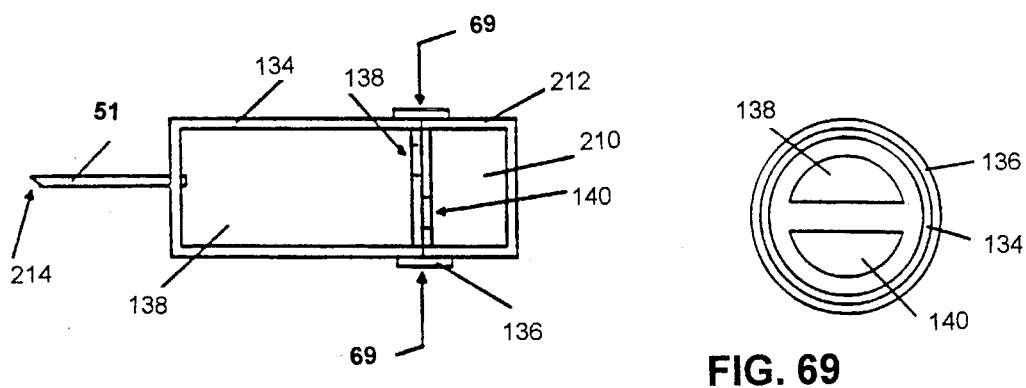
FIG. 68  FIG. 69
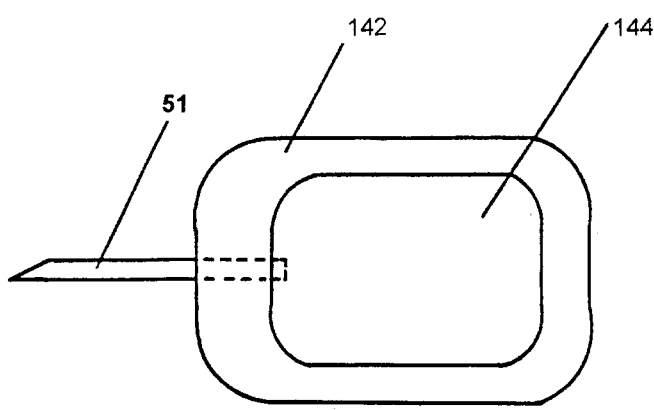 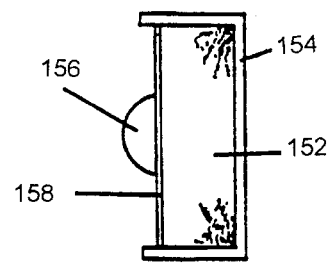
FIG. 70  FIG. 71
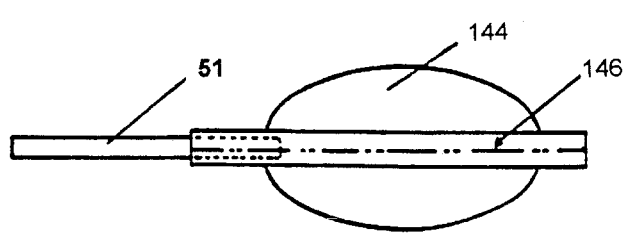 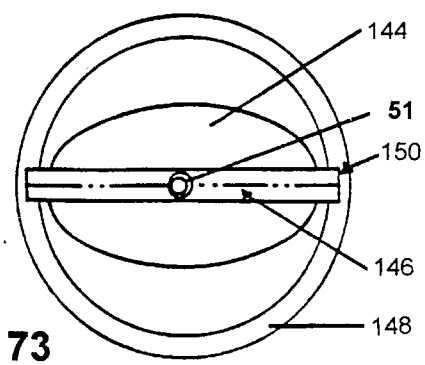
FIG. 72  FIG. 73

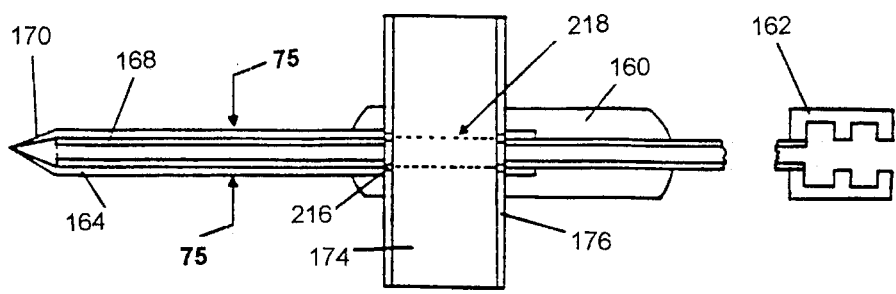
FIG. 74
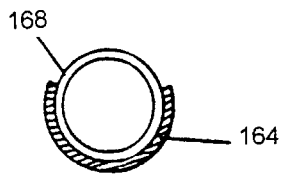
FIG. 75
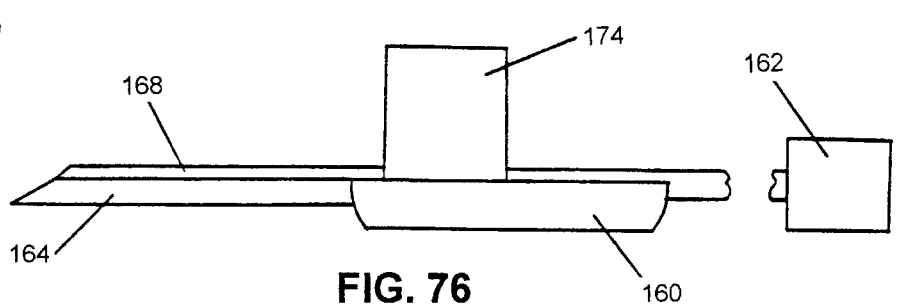
FIG. 76
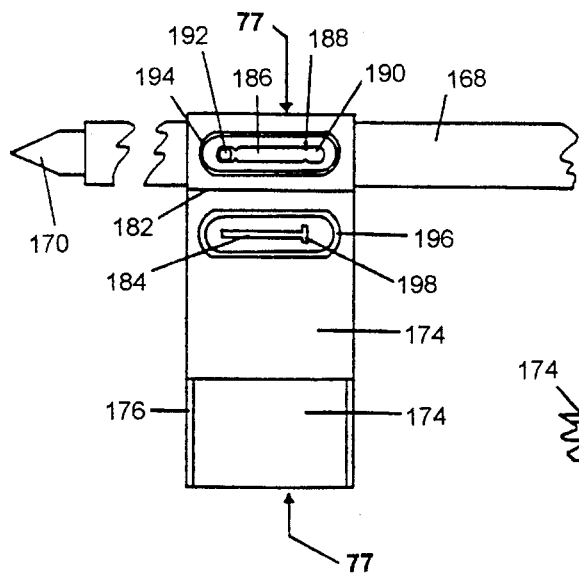
FIG. 77
FIG. 78
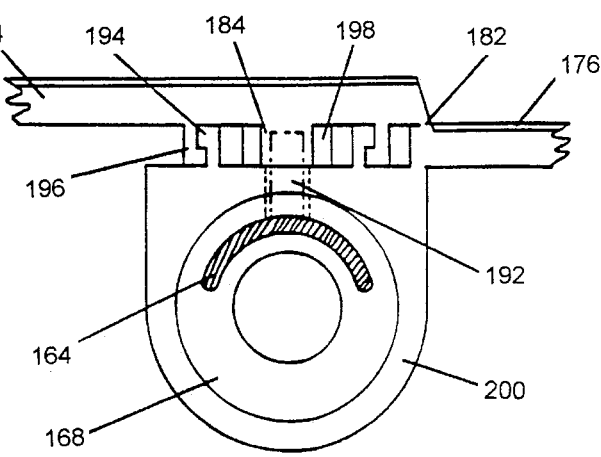

AUGMENTED POLYMERIC HYPODERMIC DEVICES

RELATED APPLICATION

This application is a continuation of U.S. patent application Ser. No. 08/120,657 filed Sep. 13, 1993, now abandoned which is a continuation-in-part of U.S. patent application Ser. No. 07/754,457 filed Sep. 3, 1991, now abandoned.

BACKGROUND OF THE INVENTION

1. Field of the Invention

This invention generally relates to hypodermic devices and, more particularly, is concerned with augmented polymeric hypodermic devices and their methods, use and manufacture.

2. Description of the Prior Art

Metal hypodermic needles and lancets have not changed substantially in over 100 years. They have many disadvantages. The foremost, is that they are dangerous. They are involved in the transmission of such deadly diseases as AIDS through inadvertent "needle sticks" of health care workers. Currently the risk is an unacceptable 1 in 200. In addition, the metal needles can break during use, requiring surgery to remove. Further, the metal needles and lancets are extremely difficult to destroy. Even segments or stubs of the needles and lancets are dangerous. They are not combustible by ordinary means and, thus, pose a continuing disposal and health problem.

Others have made many attempts to solve these problems. Their proposed solutions have taken two main routes. The first, is a substitution of plastic for metal in the needle material. The second, is a guard to shield the needle. Both avenues have failed for a variety of reasons. Plastic has not replaced metal because thin plastic needles that are hard enough to puncture the skin are too brittle and shatter, while more flexible needles lack the requisite stiffness to pierce the skin. Previous needle guards have proven to be either unwieldy, too costly, inconvenient to use or ineffective.

The following patents are included for reference as to the state of the prior art at the time of this application.

A plastic hypodermic needle that attempts to mimic the shape and function of a conventional metal needle is described by U.S. Pat. No. 2,512,568 to Saffir. U.S. Pat. No. 2,512,569 also to Saffir illustrates metal and other hard materials used only on the tip of the plastic needles to facilitate skin puncture, much as metal arrowheads are put on wooden shafts. U.S. Pat. No. 2,954,768 to Hamilton shows plastic needles with unusual piercing tip configurations. U.S. Pat. No. 3,831,814 to Butler shows another large plastic needle with unusual tip geometry. A plastic hypodermic needle with angled side portals is revealed by U.S. Pat. No. 4,838,877 to Massau.

A closed, triangular cross section, metal hypodermic needle is shown in U.S. Pat. No. 3,090,384 to Baldwin et al.

U.S. Pat. No. 4,475,906 to Holzner shows a standard hypodermic needle attached to an ampule with either a pressure seal or a breakable seal in the ampule. U.S. Pat. No. 4,548,601 to Lary reveals a standard needle with an ampule that is pierced by the rear of the needle to release the injectate.

Spring biased shields for conventional metal needles are shown by the following U.S. Pat. Nos.: 2,674,246 to Bower; 2,876,770 to White; 3,134,380 to Armao; 4,416,663 to Hall; 4,507,118 to Dent; 4,664,654 to Strauss; 4,795,432 to Karczmer; and 4,929,237 to Medway.

To guard conventional metal needles, hand operated shields which slide into different positions on the hypodermic syringe body are shown in U.S. Pat. Nos.: 4,695,274 to Fox; and 4,702,738 to Spencer.

U.S. Pat. No. 3,884,230 to Wulff describes a conventional metal hypodermic needle mounted on a flexible sleeve and surrounded by a biased spring assembly for inoculating livestock.

A resilient foam rubber or plastic biased guard of a conventional metal needle is shown by U.S. Pat. No. 4,775,369 to Schwartz. U.S. Pat. No. 4,883,068 to Dechow illustrates a blood sampling device which uses resilient foam or springs for biasing and sequencing functions of conventional metal needles.

Needle sheaths for extremely long conventional metal hypodermic needles, mainly for cervical area injections, are shown in U.S. Pat. Nos.: 3,356,089 to Francis; and 3,406,687 to Moyer.

No matter what the precise merits of the preceding, cited patents, none anticipates this invention.

SUMMARY OF THE INVENTION

This invention solves the problems presented by conventionally used metal hypodermic needles and lancets by augmenting polymeric hypodermic needles and lancets. A flexible polymeric hypodermic needle or lancet is stiffened and made to more readily pierce the skin by working in conjunction with an augmenting structure. The resultant augmented polymeric hypodermic devices have the following advantages:

1. They can be made in smaller diameters, resulting in less pain, without fear of breakage.

2. They can be made with conical points which create less tissue damage, again causing less pain and faster healing.

3. They can be made with a frangibly sealed piercing tip that makes possible a revolutionary change in prefilled ampules and phlebotomy devices.

4. The needles can be made clear or light transmissive to permit the blood or medication within to be viewed.

5. They can be made with integral safety guards to lessen the spread of such deadly diseases as AIDS.

6. They can be used with new intravenous catheter devices that will be easier and safer to insert.

7. They are less costly to manufacture than conventional hypodermic devices.

8. Unlike metal needles and lancets, these can be destroyed or rendered harmless by incineration, thus reducing contamination and disposal problems.

Many inventions have been inspired by nature. The sticking of burrs to clothing was the inspiration for "Velcro". It can be argued that metal hypodermic needles mimic the fangs of a snake. The initial inspiration for this invention possesses the least painful skin piercer and the most efficient blood extractor in nature—the mosquito. A microscopic examination of the structure of the mosquito which actually "sucks" the blood, the stylet, reveals that it is too fragile to alone puncture the skin. It must be supported by the labium in order to function. Herein is the secret of the mosquito. To clearly illustrate the advantage of this invention over metal hypodermic devices, it is only necessary to look at their respective inspirations from nature and ask the simple question, "Which causes less pain and fear—a mosquito or a snake?"

The polymeric hypodermic needle or lancet of this invention will not by itself readily puncture the skin. Like the stylet of the mosquito, it must be stiffened or supported by an augmenting means. The augmenting means is slidably or integrally engaged. Together, synergistically, they form augmented polymeric hypodermic devices. Together, they succeed where plastic needles alone have, in the past, failed. It must be emphasized that metal needles and lancets will pierce the skin unaided. Regardless of how many pads, be they called guards, guides or whatever, are associated with the metal needle or lancet, the needle or lancet will pierce the skin by itself.

Continuing the history of this invention, the slidably engaged structure—a support and guide—logically evolved into possessing other features such as safety guard and positional safety guard. These were not added on features as in the case of safety guards for metal needles. Metal needles do not need guides or guards in order to puncture the skin. In fact, it is the purpose of safety guards on metal needles to stop them from puncturing the skin. However, with augmented polymeric hypodermic devices, the guides and/or guards, at the proper moment, make puncturing possible.

In order to provide more pinpoint accuracy for injections and to allow deeper penetration of the needle, a second method of augmenting a polymeric hypodermic needle was developed. This involved an integral stiffening and/or support structure. Such a needle was augmented, but did not require a separate augmenting means in order to function. Although the same type of safety guard could be used with this integrally augmented needle, it could pierce the skin alone.

A microscopic examination of the tip of a conventional metal needle will reveal an interesting fact that, previously, has not been appreciated. It is only the extreme tip of the needle and only a portion of the sides depending from the tip that actually puncture and cut the skin. The rest, the upper parts of the sides and the arcuate top just come along for the ride. In fact, those segments of the needle tip present a resistance to penetration. The gouging of the tissue by those segments is called "coring" and results in tissue damage and slow healing.

It is believed that since the present conventional hypodermic needle is already functioning as if it were two parts, a tip that punctures and a tube that transports fluids, why not really make it of two parts. It then became a search for designs for each part that would perform better alone and synergistically than the present style of needle. An open trough or "V" shaped puncturing part was selected as ideal. Previous research has shown that "V" shaped needles require less force to puncture the skin than do conventional round needles. Further, a "V" shape would lend itself to unhardened metals, and composite materials, as well as to hardened stainless steel. A "V" shape could also be formed with a novel, plow shaped structure at the tip which would separate and push aside the tissue to reduce coring. The tube to transport the fluids could be either a separate cannula or it could be a covering like structure that simply closed off the open side of the "V".

In either case, the plastic tube or covering led to a frangible seal at the tip. This was the breakthrough that ampule designs have needed. The two, previously tried solutions to keeping the medicament in the ampule have serious flaws. The first is a rear seal which tends to introduce air bubbles ahead of the medicament. The second is a tip which is plugged with a biocompatible material that is injected along with the medicament. The frangible seal at the tip solves both problems by preventing air bubbles and extraneous matter from being injected with the medicament.

Of course, other materials from which the devices can be manufactured have been brought in, such as ceramics, minerals such as silicates and boron and carbon fibers, and composites which besides the materials just mentioned employ plastics and metals in various degrees of hardness and cross sectional shapes such as wire, plates, channels, "V", arcuate and foil. In most of the designs, the light transmissive polymeric component permits the blood, body fluid, or medicament to be visible over the entire length of the hypodermic needle, a dramatic improvement over metal needles.

The new frangible seal contributes to a vast improvement in phlebotomy. It gives two main advantages over the present technology. The first is a safety feature, as there is no rearward projecting needle that is unguarded. The second, is that it requires only one hand to operate rather that the two needed for the conventional blood drawing devices.

And, finally, it was reasoned, why should the polymeric hypodermic cannula be permanently attached to the piercing structure? This idea led to a significant improvement in the method for inserting intravenous catheters. In the present method, after the needle-cannula is inserted, the needle is withdrawn with one hand, causing blood to squirt or ooze from the cannula, while the other hand races to connect a line and thus stop the blood flow. In this invention, the transporting cannula is connected to the line before insertion into the skin, which prevents blood leakage. Since the cannula is clear, it is easier to correctly position the catheter in a vein. The arcuate or "V" shaped piercing structure is easily withdrawn or retracted without disturbing the cannula.

This invention teaches new devices which will make the removal of body fluids and the injection of medicaments less painful, less costly, more safe, and the by-products easier to dispose.

BRIEF DESCRIPTION OF THE DRAWINGS

FIGS. 10 through 12 are perspective views of different tip angles of hollow needles.

FIGS. 13 through 17 are elevational side views of frangibly sealed hollow needle tips.

FIGS. 18 and 19 are schematic side views of different lancet tip angles.

FIG. 28 is a schematic side view of the augmented polymeric hypodermic device with slidable guard and lancet.

FIG. 29 is a schematic side view of an augmented polymeric hypodermic device with slidable guard and hollow needle.

FIG. 30 is a schematic side view of an augmented polymeric hypodermic device with slidable guard, external base support and lancet.

FIG. 31 is a schematic side view of an augmented polymeric hypodermic device with slidable guard, external base support and hollow needle.

FIG. 32 is a schematic top view of a hollow needle with a filler material.

FIG. 33 is a schematic top view of a hollow needle made from a wrapped plastic film.

FIG. 34 is a schematic top view of a hollow needle made from a wrapped plastic film and a hard filler material.

FIGS. 35 through 48 are schematic top views of various hollow needle designs with integral stiffening and/or piercing structure(s).

FIG. 49 is a cross sectional view of FIG. 41.

FIG. 50 is a perspective side view of an open tip, triangular shaped, integrally stiffened, hollow needle.

FIG. 51 is a perspective side view of a frangibly sealed, triangular shaped, integrally stiffened, hollow needle.

FIG. 52 is a schematic side view of an augmented polymeric hypodermic device with an integral support, slidable guard, needle pinch and hollow needle.

FIG. 53 is a cross sectional view of FIG. 52.

FIG. 54 is an enlargement of FIG. 52 showing the needle pinch in the closed position.

FIG. 55 is an alternate cam needle pinch.

FIG. 56 is a schematic view of the manufacturing process.

FIG. 67 is a schematic side view of an augmented polymeric hypodermic device with an enclosed test strip that is used in phlebotomy.

FIG. 68 is a schematic side view of an augmented polymeric hypodermic device with an enclosed reagent that is used in phlebotomy.

FIG. 69 is a cross sectional view of FIG. 68.

FIG. 70 is a schematic top view of an augmented polymeric hypodermic device used as a prefilled ampule.

FIG. 71 is a schematic side view of the end cap for the container shown in FIG. 73.

FIG. 72 is a schematic side view of FIG. 70.

FIG. 73 is a schematic end view of the device of FIG. 72 enclosed in a protective container.

FIG. 74 is a schematic top view of an augmented polymeric hypodermic device with removable piercing member used as an intravenous catheter.

FIG. 75 is a cross sectional view of FIG. 74.

FIG. 76 is a schematic side view of FIG. 74.

FIG. 77 is a cross sectional view of FIG. 78.

FIG. 78 is a schematic top view of an augmented polymeric hypodermic device with a retractable piercing member used as an intravenous catheter.

DETAILED DESCRIPTION OF THE INVENTION

Figure 1:
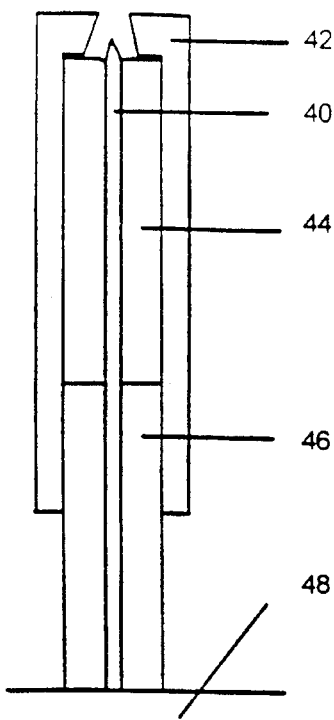
FIG. 1 is a schematic side view of the augmented polymeric hypodermic device with slidable guard and lancet.

Augmented polymeric hypodermic devices can take several forms. They can be most broadly characterized by the piercing member. First, there are flexible piercing members which require separate, slidably engaged augmenting means in order to perform the piercing process. Second, there are integrally augmented piercing members which can perform the piercing process alone. Third, there are intravenous catheter devices which employ a slidable piercing member which is either removably or retractably engaged to the polymeric cannula.

First, the augmented polymeric hypodermic devices which use a flexible piercing member will be discussed. These are comprised of essentially three parts: a polymeric, flexible piercing member with a piercing tip; an augmenting means to stiffen the piercing member sufficiently so that together they can perform the piercing process; and a supporting base structure to which the piercing member is attached and which supports the augmenting means.

The flexible, polymeric piercing member can be either one of two broad classes: a solid lancet; or a needle with at least one lumen. The piercing tip can be either one of three broad classes: a solid lancet tip; a hollow needle tip; or a frangibly sealed hollow needle tip. The angle of the tip can be either: flat; oblique; compound; or conical. The flexible, polymeric piercing member can be extruded from a suitable plastic such as a polycarbonate, although other polymeric materials can also be used. The plastic can be transparent or light transmissive to allow the blood or medicament within to be viewed. The plastic can be virgin, or recycled material, or it can have additives such as glass or carbon fibers for strength and hardness. All of the devices described are burnable.

The augmenting means can comprise one or more parts. All of the parts slide in relationship to the piercing member. The augmenting means is at least partly about the piercing member. The augmenting means stiffens the piercing member. It slides in relationship to the piercing member so that it can expose the piercing tip from the guarded position and allow the piercing member to complete the piercing process. The augmenting means continues to stiffen the piercing member as it slides. The augmenting means is supported by the supporting base structure.

The supporting base structure can be relatively flat or it can have one or more projections. When it is flat, then the augmenting means rests on its surface. The augmenting means can also be attached either fixedly or removably. When the supporting base structure has a projection(s) then at least one part of the augmenting means slides either on or in relation to that projection(s). The piercing member can be attached to the supporting base structure by one or a combination of several methods such as: adhesive; solvent; heat; or by molding. The supporting base structure can be very simple as in the case of a polymeric hypodermic lancet, in which the lancet is merely attached. However, the supporting base structure for the polymeric hypodermic needle can take many forms, as it is the function of the lumen(s) of the polymeric needle to transfer generally liquid material. Therefore, the supporting base structure must be of a shape that is either part of a reservoir itself or can be attached to a reservoir. A reservoir is something, such as a syringe or an ampule, which can hold a generally liquid material. The reservoir does not have to be plastic. The supporting base structure can also be a means of attachment to a syringe such as a hub, a terminal end of medical tubing or any other means of attachment to a reservoir. Besides being used for injections, blood sampling and other uses for humans the devices can also find a wide use in veterinary medicine.

The following will expand on the general description stated above with a detailed explanation of the drawings.

In one preferred embodiment of the device as shown in FIG. 1, the slidable guard (42) is in slidable proximity to supporting base projection (46) to which the polymeric hypodermic lancet (40) is attached. The slidable guard (42) is also in slidable relationship to the polymeric hypodermic lancet (40). The slidable resilient foam (44) restrains the sideways flexure of the polymeric hypodermic lancet (40) as it slides in relation to the lancet while it is itself being contained and compressed by the slidable guard (42) during the piercing process. These two, slidable guard (42) and slidable resilient foam (44) work together synergistically to make an augmenting means that makes it possible for the polymeric hypodermic lancet (40) to pierce the skin, a function that the lancet would otherwise be unable to do unaided. The supporting base projection (46) is either attached to or is an integral molded part of the supporting base structure (48). The supporting base structure (48) is here represented in its simplest form. The means of attaching the lancet to the base can be selected from any of the designs as shown in FIGS. 20 through 23. The slidable guard (42) and the supporting base structure (48) and supporting base projection (46) can be made from an inexpensive polystyrene; the polymeric hypodermic lancet (40) from a polycarbonate; and the slidable resilient foam (44) from a foam rubber or a polymeric foam such as a polyurethane. The composition of these parts is, however, not limited to the above mentioned materials. The factors which determine material selection are functionability, coupled with reasonable cost and ease of manufacture. The slidable guard (42) and the supporting base structure (48) and supporting base projection (46) can be made by injection molding; the polymeric hypodermic lancet (40) by extrusion; and the slidable resilient foam (44) by extrusion or cut from sheet stock with dies like doughnuts or it can be cut in parallelograms that are subsequently rolled and fused with heat, solvent or adhesive along one side to form a tube. The polymeric hypodermic lancet (40) is given a sharpened tip as shown In one of the FIGS. 18 or 19 by a mechanical process such as shearing or grinding, or by a heat method such as a laser. The polymeric hypodermic lancet (40) is attached to the supporting base structure (48) and supporting base projection (46) by an adhesive, by solvent, or by heat, or the supporting base structure (48) and supporting base projection (46) are molded around the polymeric hypodermic lancet (40). The supporting base structure can also be molded of two or more parts and then attached to the lancet by one of the previously described methods. The supporting base projection (46) can be molded as an integral part of the supporting base structure (48) or it can be molded separately and then attached to the supporting base by heat, solvent or adhesive.

Figure 2:
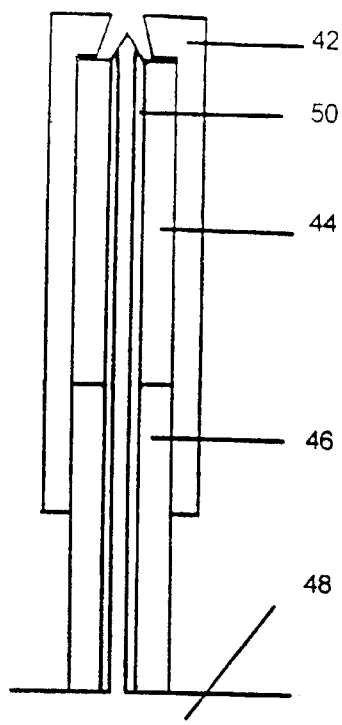
FIG. 2 is a schematic side view of the augmented polymeric hypodermic device with slidable guard and hollow needle.

FIG. 2 is identical to FIG. 1 with the exceptions that a polymeric hypodermic needle (50) with a piercing tip and at least one lumen replaces the lancet and the needle is attached to the supporting base structure (48) which has a corresponding hole so that generally fluid material can pass through. The supporting base structure is selected from one of the FIGS. 24 through 27. The supporting base structure (48) can be a hub for attaching a needle to a syringe such as a "Luer" type or one of several snap-on designs. The supporting base structure can also be an integral part of a one-piece syringe or ampule or other medical hypodermic device. The piercing tip is selected from one of the FIGS. 10 through 17, which includes the frangibly sealed tips that will be described later.

Figure 3:
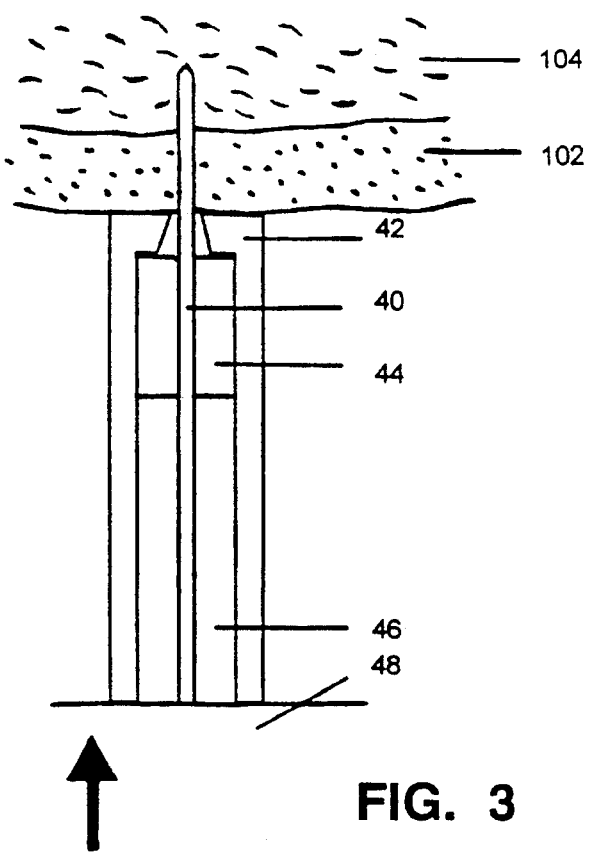
FIG. 3 is a schematic side view of the augmented polymeric hypodermic device of FIG. 1 with slidable guard and lancet in use, piercing the skin and underlying subcutaneous tissue.

In FIG. 3, the polymeric hypodermic lancet device of FIG. 1 is illustrated after completing the piercing process. Skin (102) and subcutaneous tissue (104) are shown after being pierced. During the piercing process, force is exerted—as represented by the black arrow pushing the rear of the augmented polymeric hypodermic device. This causes the slidable guard (42) to come in contact with skin (102) and then to be pushed against and compress the slidable resilient foam (44). As the polymeric hypodermic lancet (40) is pushed through skin (102) and into the subcutaneous tissue (104), the slidable resilient foam (44) restrains the sideways flexure of the lancet thereby stiffening it sufficiently to make the piercing process possible. The depth of the piercing process can be controlled by the distance that the slidable guard (42) can travel before being stopped by making contact with the supporting base structure (48). If this distance is greater, then the lancet (40) will pierce deeper. If the distance is less, then the lancet will make a shallower puncture. The slidable guard (42) is guided by and slides on the supporting base projection (46). During the piercing process the slidable resilient foam (44) is compressed between the slidable guard (42) and the supporting base projection (46). In the "at rest" position, before the piercing process begins, the slidable resilient foam (44) is not under compression so there is no tendency for the device to come apart. Friction holds the slidable guard (42) to the supporting base projection (46). After the piercing process has been completed, the device is destroyed by burning, solvents, shredding, grinding, or a combination of these simple destructive means.

It should be obvious that the piercing process for the polymeric hypodermic needle device of FIG. 2 will be the same. The only difference is that substantially liquid material can be extracted or injected through the lumen of the needle which extends through the supporting base structure (48). In the special case of the polymeric hypodermic needle device of FIG. 2 with a frangibly sealed piercing tip, after the piercing process is complete, then other pressure is exerted on the liquid material in the syringe or ampule thereby breaking the frangibly sealed piercing tip and expelling the material through the lumen of the needle into the subcutaneous tissue.

Figure 4:
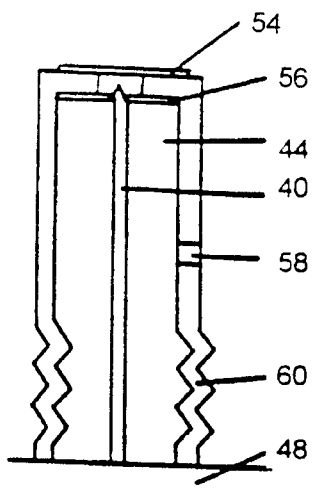
FIG. 4 is a schematic side view of the augmented polymeric hypodermic device with a slidable collapsible guard and lancet.

In another preferred embodiment of the device as shown in FIG. 4, slidable collapsible guard (60) makes a supporting base projection unnecessary, Slidable resilient foam (44) is injected through hole (58). It is restrained from oozing out by disk (56). Seal (54) provides asepsis. FIG. 4 shows the polymeric hypodermic lancet (40) model of this style. All of the lancet tip and lancet supporting base structure designs can be used with this model.

Figure 5:
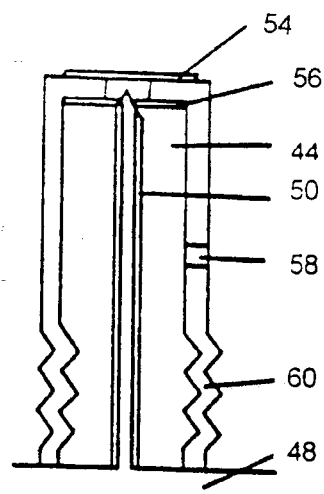
FIG. 5 is a schematic side view of the augmented polymeric hypodermic device with a slidable collapsible guard and hollow needle.

FIG. 5 shows the polymeric hypodermic needle (50) version. Again, the difference between the two models is that the polymeric hypodermic needle (50) has at least one lumen as described previously. The lumen of the needle mates with a corresponding hole in the supporting base structure. The polymeric hypodermic needle (50) of FIG. 5 can also have a frangibly sealed tip as previously described as well as any of the other needle tip and needle supporting base structure designs.

Figure 6:
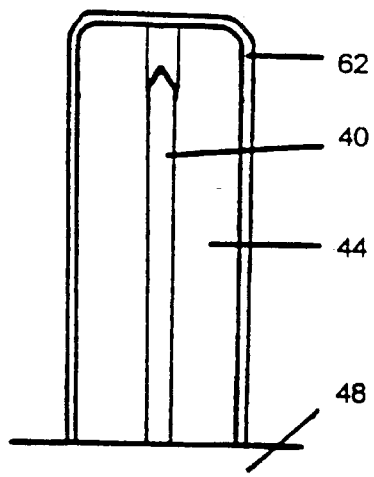
FIG. 6 is a schematic side view of the augmented polymeric hypodermic device with a slidable shrink wrap guard and lancet.

In another preferred embodiment of the device as shown in FIG. 6, slidable resilient foam (44) is held in place and asepsis is provided by slidable shrink wrap guard (62) which encloses slidable resilient foam (44) while it maintains asepsis. During the piercing process, the polymeric hypodermic lancet (40) pierces the slidable shrink wrap guard (62); the slidable resilient foam (44) is compressed thereby stiffening the polymeric hypodermic lancet (40). The slidable resilient foam (44) is made so that it extends past the end of the polymeric lancet (40) so that the slidable shrink wrap guard (62) can be placed over the slidable resilient foam (44) without being prematurely pierced by the polymeric hypodermic lancet (40). The polymeric hypodermic lancet (40) and the slidable shrink wrap guard (62) are attached to the supporting base structure (48) which supports the slidable resilient foam (44). Any of the other lancet tip and lancet supporting base structures can be employed with this model. This is one of the least expensive of the designs to manufacture. It readily lends itself to testing procedures where a one time use, easily disposable blood sampling lancet is desired.

Figure 7:
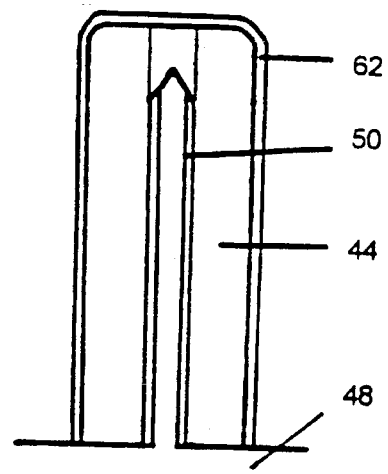
FIG. 7 is a schematic side view of the augmented polymeric hypodermic device with a slidable shrink wrap guard and hollow needle.

FIG. 7 illustrates the polymeric hypodermic needle (50) version of this model. The polymeric hypodermic needle (50) does not become clogged as it pierces the slidable shrink wrap guard (62), as long as the piercing tip geometry of the hollow needle design is oblique or compound as illustrated in FIGS. 11 or 12 respectively. Of course, if the piercing needle tip is selected from one of the frangibly sealed models as shown by FIGS. 13 through 17, then it can't become clogged. Again, the lumen of the needle extends through a corresponding hole in the supporting base structure. Any of the other needle tip and needle supporting base structure designs can be used with this device.

Figure 8:
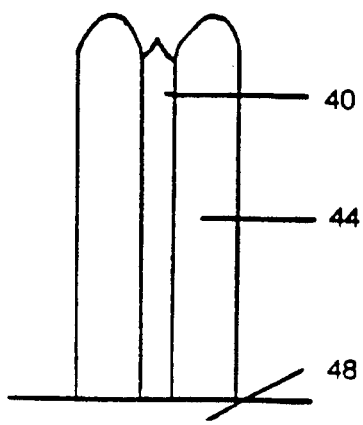
FIG. 8 is a schematic side view of the augmented polymeric hypodermic device with slidable resilient foam and lancet.

In another preferred embodiment of the device as shown in FIG. 8, slidable resilient foam (44) alone stiffens the polymeric hypodermic lancet (44). The supporting base structure (48) and the means of attaching the polymeric hypodermic lancet (40) can be selected from any of those shown in FIGS. 20 through 23. The lancet piercing tip design can be selected from those shown in FIGS. 18 and 19. This model makes a one-time use device that is inexpensive to manufacture and easy to dispose.

The design of FIG. 8 can also be made with a polymeric hypodermic needle (50) in place of the polymeric hypodermic lancet (40) and with the lumen of the needle extending through the supporting base structure (48). The supporting base structure (48) and the means of attachment of the polymeric hypodermic needle (50) can be selected from any of FIGS. 24 through 27. This design can also be made with any of the hollow needle piercing tip designs, including a frangibly sealed piercing tip, selected from FIGS. 10 through 17.

Figure 9:
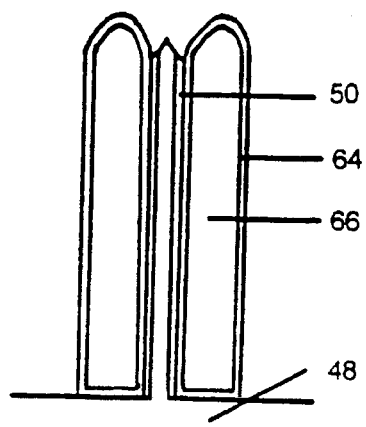
FIG. 9 is a schematic side view of the augmented polymeric hypodermic device with slidable compressible ring and hollow needle.

FIG. 9 illustrates a model with a slidable compressible ring (64) which fits like a doughnut around the polymeric hypodermic needle (50) to stiffen it during the piercing process. The polymeric hypodermic needle (50) is attached to the supporting base structure in any one of the ways shown in FIGS. 24 through 27. The piercing tip of the polymeric hypodermic needle (50) is selected from any one of the designs as shown in FIGS. 10 through 17, including the frangibly sealed tip models. The slidable compressible ring (64) is attached to the supporting base structure (48) and is made from a plastic material such as polyethylene which is at least partially filled with a material (66) which is selected from the list of: resilient foam; gas; a specific gas, such as nitrogen; liquid; a specific liquid such as distilled water. During the piercing process, the slidable compressible ring (64) is compressed thereby simultaneously exposing the piercing tip and stiffening the polymeric hypodermic needle (50). The material (66) is selected to provide support for the slidable compressible ring (64) so that the ring will compress in a controlled and predetermined manner to facilitate the piercing process.

The embodiment of FIG. 9 can also be made with a polymeric hypodermic lancet (40) in place of the needle. The supporting base structure (48) and the means of attaching the polymeric hypodermic lancet (40) can be selected from any of those shown in FIGS. 20 through 23. The piercing tip design can be selected from either one of FIGS. 18 or 19.

FIGS. 10 through 12 show perspective views of various tip geometries for the polymeric hypodermic needle (50). The preferred embodiments are FIGS. 11 and 12, oblique and compound angles respectively. The tips are cut with a mechanical means such as shearing or grinding or laser or other heat source. The preferred material for the needles is a polycarbonate processed by a twin-screw extruder to reduce heat degradation of the plastic.

FIGS. 13 through 17 show various frangibly sealed polymeric hypodermic needle tip designs. FIG. 13 shows a frangibly sealed needle tip with an oblique angle. FIG. 14 shows a different elevational view of FIG. 13. FIG. 15 shows a frangibly sealed polymeric hypodermic needle tip with a compound angle. FIG. 16 shows a different elevational view of FIG. 15. The needle tip is pinched together and frangibly fused, glued or solvent welded and cut. The frangibly sealed needle tip (68) is frangibly sealed at junction (70). In the frangible fusing process, heat in the form of a laser or other heat source is applied as the polymeric hypodermic needle (50) is being pinched together. The width and depth of the seal and, therefore, the strength of the seal can be controlled by the length of time, amount of pressure and degree of heat that is applied to the needle. Different plastics require different combinations of time, pressure and heat. Thickness of the needle wall in relation to needle diameter plays an important part. The laser can also perform the cutting process or the needle can be cut with a mechanical process such as shearing. In the gluing or solvent welding process, pinching pressure is maintained while the adhesive or solvent is applied and allowed to cure. Again, length of time and pressure as well as adhesive or solvent applied determine the strength of the breakably sealed needle tip. In FIG. 17, circular area (72) has been weakened by a laser that has reduced the thickness by melting or burning the polymeric material in that area. The frangible seal which is created at junction (70) or weakened circular area (72) is such that it will break or open when sufficient internal pressure is exerted within the polymeric hypodermic needle (50) during the injection process by the medicament being forced out of the syringe or ampule.

FIGS. 20 through 27 illustrate how the piercing member is attached to the supporting base structure. Either the lancet (40) or the needle (50) is attached by adhesive, solvent, heat or the supporting base structure (48) is molded around the piercing member at the attachment zone (74). The heat for bonding at the attachment zone (74) can be supplied by a heat source such as a laser. The attachment zone (74) also can represent the place where the supporting base structure (48) is molded around the piercing member. In the case of molding, the supporting base structure can be molded from one or more parts. The piercing member is attached to the walls of the hole which is sized to receive it in the supporting base structure.

Figure 20:
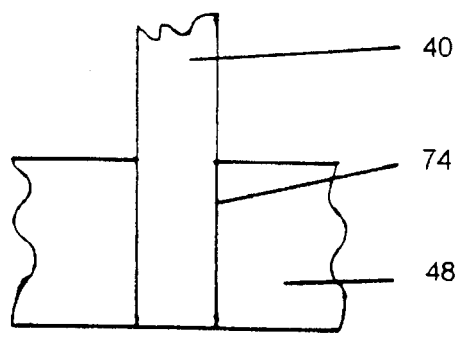
FIGS. 20 through 23 are schematic side views of different means of attaching a lancet to a supporting base structure.
Figure 22:
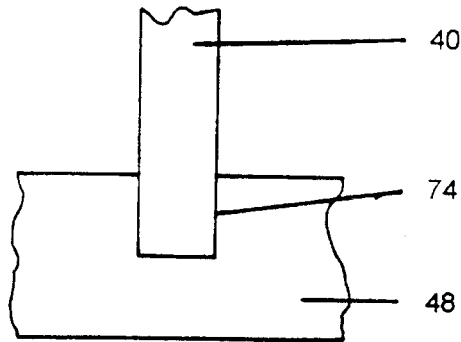
Figure 21:
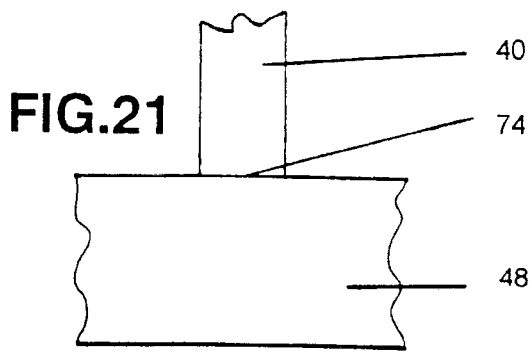
Figure 23:
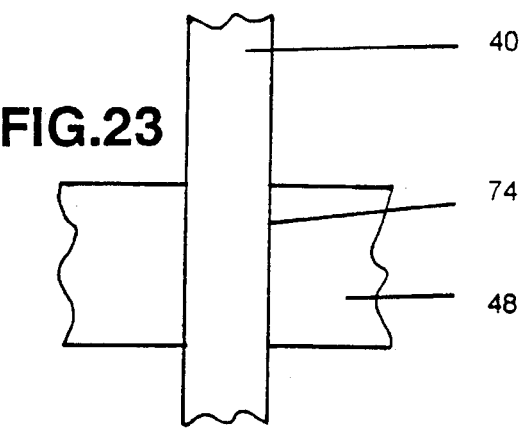

FIGS. 20 through 23 show polymeric hypodermic lancets attached to a supporting base structure. In FIG. 20 the polymeric hypodermic lancet (40) extends completely through the supporting base structure (48) and is flush with the opposite side. In FIG. 23 the polymeric hypodermic lancet (40) extends past the opposite side of the supporting base structure (48). In FIG. 22 the polymeric hypodermic lancet (40) is attached to the walls of a hole which is sized to to receive it in the supporting base structure (48). In FIG. 21 the polymeric hypodermic lancet (40) is attached to the surface of the supporting base structure (48). FIG. 21 is the only one of the four FIGS. where molding is not an option for the means of attachment.

Figure 24:
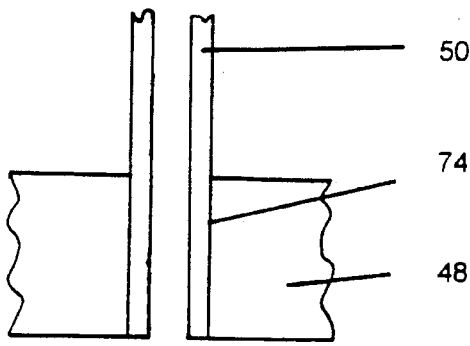
FIGS. 24 through 27 are schematic side views of different means of attaching a hollow needle to a supporting base structure.
Figure 26:
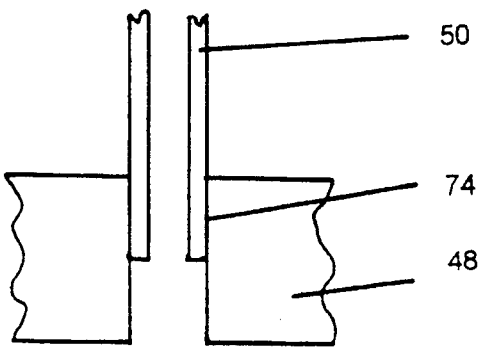
Figure 25:
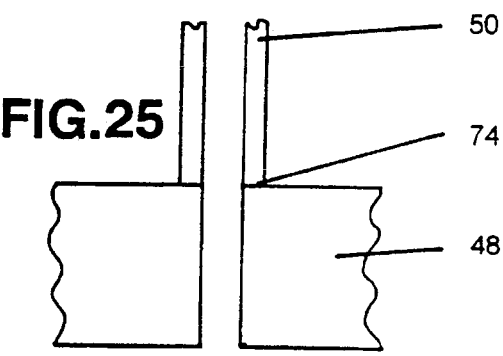
Figure 27:
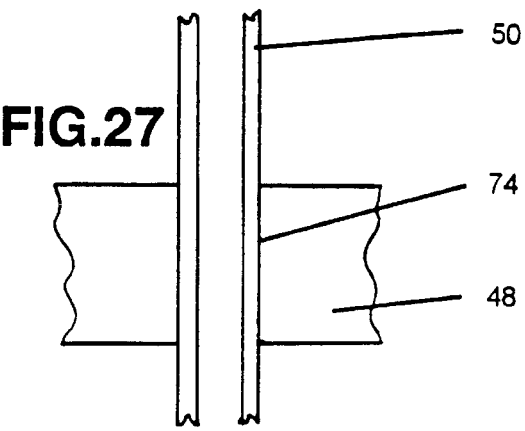

In FIGS. 24 through 27 a polymeric hypodermic needle (50) is attached to the supporting base structure (48) at the attachment zone (74) and a lumen extends completely through the base. The means of attachment is as stated above. FIG. 24 shows a polymeric hypodermic needle (50) extending through the supporting base structure (48) so that the needle is flush with the opposite side of the base. FIG. 27 shows the polymeric hypodermic needle (50) extending past the opposite side of the supporting base structure. FIG. 26 shows the polymeric hypodermic needle (50) partly within a hole sized to receive it in the supporting base structure. FIG. 25 illustrates the polymeric hypodermic needle (50) attached to the surface of the supporting base structure (48) so that the lumen of the needle corresponds with a hole in the base. FIG. 25 is the only one of the four FIGS. in which molding is not an option for the means of attachment of the needle to the base.

FIGS. 28 through 31 illustrate augmented polymeric hypodermic devices in which the close-fitting slidable guard (76) itself partially restrains the sideways flexure of either the polymeric hypodermic lancet (40) or the polymeric hypodermic needle (50), thereby stiffening it to facilitate the piercing process. The slidable resilient foam (44) also partially restrains the sideways flexure of the piercing member as it is being compressed by the close-fitting slidable guard (76). The external base supports (78) provide additional support for the devices shown in FIGS. 30 and 31. The lancet devices of FIGS. 28 and 30 can be used with any of the supporting base structures (48) as shown in FIGS. 21 through 23 and any of the lancet tips shown in FIGS. 18 or 19. The needle designs of FIGS. 29 and 31 can be used with any of the supporting base structures (48) that are shown in FIGS. 24 through 27 and any of the needle tips illustrated in FIGS. 10 through 17. The lumen of the polymeric hypodermic needle (50) extends through the supporting base structure (48).

FIGS. 32 and 33 show alternate methods of making the polymeric hypodermic needle. In FIG. 32, the needle is composed of two materials—a polymeric material (80) such as polycarbonate and a filler material (82) such as glass fibers. The glass fibers add rigidity to the needle and make a harder and sharper piercing tip. The glass fibers are added during the extrusion process. This method can also be used to produce polymeric hypodermic lancets. FIG. 33 is a design for a wound needle. Polymeric film material (84) is joined at the adhesion line (86) by heat, solvent, or adhesive. This makes a stiffer needle. This method, too, can be used to produce polymeric hypodermic lancets. Either of these designs for needles and lancets can be used with any of the augmented polymeric hypodermic devices that employ a piercing member. They can be used with any of the appropriate piercing tip designs and supporting base structures.

FIGS. 52 through 55 show another augmented polymeric hypodermic device. The slidable support guard (100) which is molded in two halves has integral support flanges (102) which stiffen and guide the polymeric hypodermic needle (50). The support flanges (102) break off as they come in contact with supporting base structure (48) during the piercing process. The two halves of the slidable support guard (100) are glued or fused together. FIG. 54 shows an enlargement of FIG. 52, a clamp needle pinch (98) closes off the polymeric hypodermic needle (50) when an actuating guide on the slidable support guide (100) passes by. FIG. 55 shows an alternate cam needle pinch (104).

One of the manufacturing processes is shown in FIG. 56. The polymeric hypodermic lancet (40), made of polycarbonate, has just come from a twin screw extruder. It is handled in rolls, not individual pieces as in the case of metal lancets. Here, the supporting base structure (48) of polystyrene has been attached by molding. They can also be made from two halves which are subsequently glued or solvent or heat welded onto the lancet stock. The lancet stock is then cut at location (106) by either a mechanical, such as shearing, or heat process, such as a laser. The polymeric hypodermic needle manufacturing process is similar, with the exception that a frangibly sealed tip could be produced at location (106) rather than a straight or compound cut.

Next, one time use, augmented polymeric hypodermic devices will be discussed which relate to FIGS. 57 through 64. These devices all lock into a safe, shielded position after they have been used only once. All of the lancet models, FIGS. 57, 59 and 63, can be made with either of the piercing tips shown in FIGS. 18 or 19 and any of the supporting base structures shown in FIGS. 20 through 23. All of the needle models, FIGS. 58, 62 and 64, can be made with any of the piercing tips shown in FIGS. 10 through 17, and any of the supporting base structures shown in FIGS. 24 through 27. When the springs are plastic, then the entire device is burnable.

Figure 57:
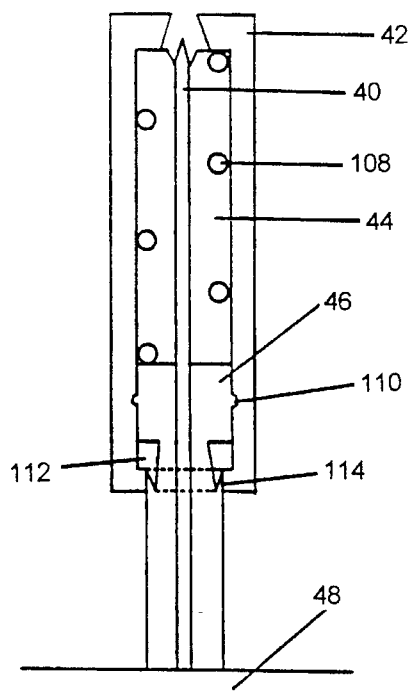
FIG. 57 is a schematic side view of an augmented polymeric hypodermic device with a one time use slidable guard and lancet.
Figure 58:
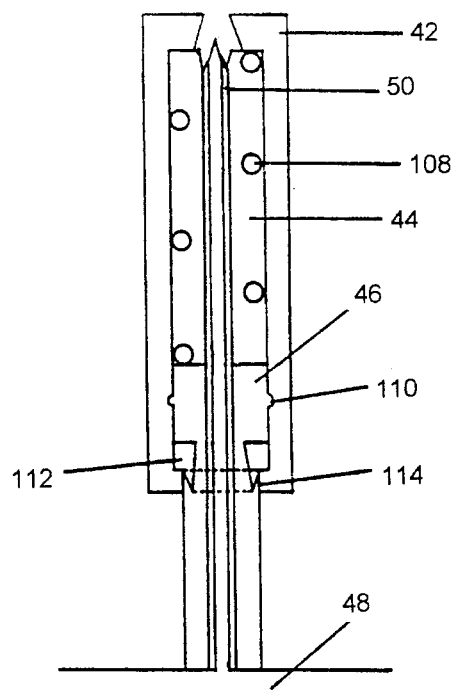
FIG. 58 is a schematic side view of an augmented polymeric hypodermic device with a one time use slidable guard and hollow needle.

The detent (110) of FIG. 57 keeps the slidable guard (42) from moving before use. After the piercing process is finished, slidable resilient foam (44) and spring (108) push the slidable guard (42) into the locking position (112) past cup-shaped self-spring (114) which stops the device from reuse. The device of FIG. 58 works the same, with the exception that a polymeric hypodermic needle (50) is used instead of a lancet. The slidable resilient foam (44) and the spring (108) can be co-extruded.

Figure 59:
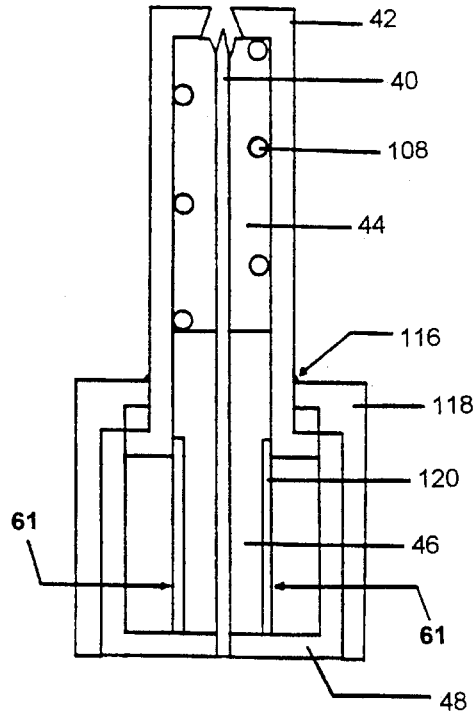
FIG. 59 is a schematic side view of an augmented polymeric hypodermic device with a one time use slidable guard and lancet.
Figure 60:
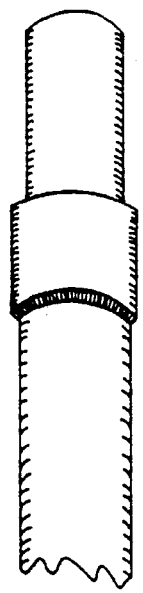
FIG. 60 is a perspective side view of FIG. 62.
Figure 61:
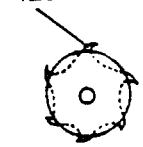
FIG. 61 is a cross sectional view of the self-spring taken through FIG. 59.
Figure 62:
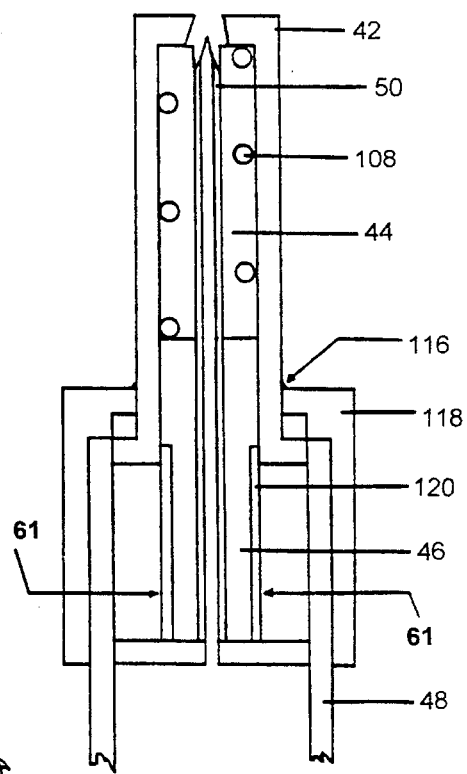
FIG. 62 is a schematic side view of an augmented polymeric hypodermic device with a one time use slidable guard and hollow needle.

The spot seal (116) of FIG. 59 keeps the slidable guard (42) from moving before use. After the piercing process is finished, slidable resilient foam (44) and spring (108) push the slidable guard (42) into the locking position past self spring ridge(s) (120) molded into supporting base projection (46) as shown in FIG. 61. Retaining ring (118) is molded as a separate piece which is attached to the supporting base structure (48). FIG. 60 illustrates a perspective view of the device shown in FIG. 62. The device of FIG. 62 works the same as FIG. 59 with the exception that a polymeric hypodermic needle (50) is used. The spring (108) and slidable resilient foam (44) can be co-extruded.

Figure 63:
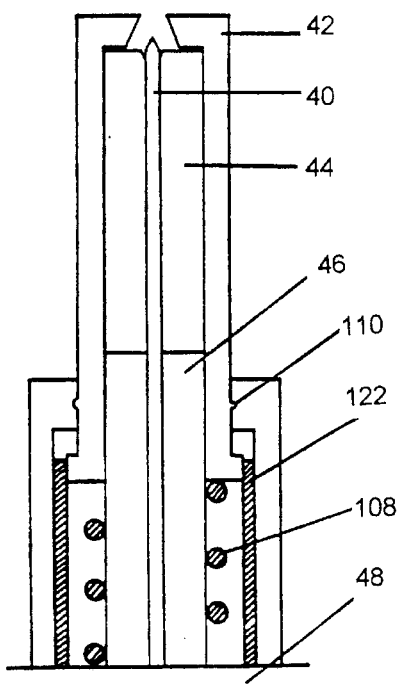
FIG. 63 is a schematic side view of an augmented polymeric hypodermic device with a one time use slidable guard and lancet.
Figure 64:
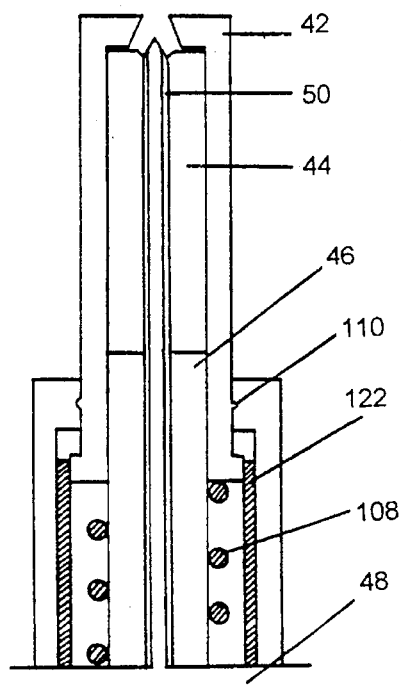
FIG. 64 is a schematic side view of an augmented polymeric hypodermic device with a one time use slidable guard and hollow needle.

The detent (110) of FIG. 63 keeps the slidable guard (42) from moving before use. After the piercing process is finished, the slidable resilient foam (44) and the spring (108) push the slidable guard (42) into the locking position past the cylindrical self-spring (122) which stops the device from being used again. The device of FIG. 64 works the same, with the exception that a polymeric hypodermic needle (50) is used in place of a lancet. When the cylindrical self-spring (122) and spring (108) are plastic, then, the entire device is burnable.

Figure 66:
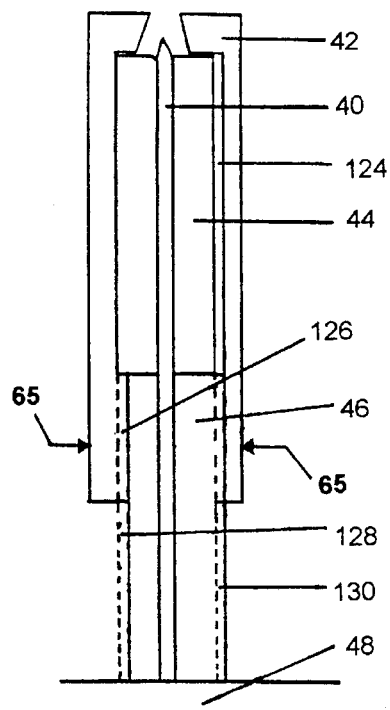
FIG. 66 is a schematic side view of an augmented polymeric hypodermic device with ridged and grooved slidable guard.
Figure 65:
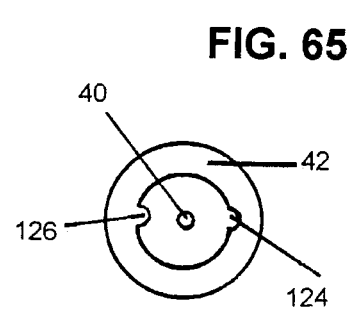
FIG. 65 is a cross sectional view of FIG. 66.

FIG. 66 shows a device similar to that of FIG. 1 with the addition of a slidable guard ridge (126) and a slidable guard groove (124) which mate with a supporting base projection groove (128) and a supporting base projection ridge (130) respectively. The cross section of FIG. 66 is shown in FIG. 65. Both ridge and groove are shown on one device for the sake of simplicity and to illustrate the principal. Only one ridge or groove is necessary to accomplish the purpose of keeping the slidable guard (42) from turning. However, more ridges and/or grooves do add more rigidity. For the sake of ease in molding and assembly, it is preferable to have all groove(s) (124) on the slidable guard and all mating ridge(s) on the supporting base projection (46). This option can also be employed on similar devices using the polymeric hypodermic needle.

Second, the augmented polymeric hypodermic devices which use an integrally augmented piercing member will be discussed. These piercing members can perform the piercing process alone. FIGS. 34 through 51 show various models of integrally augmented piercing members. These augmented polymeric hypodermic devices are comprised of essentially two parts: a polymeric component and a stiffening member which are integrally combined into an augmented polymeric piercing member with a piercing tip; and a supporting base structure to which the augmented polymeric piercing member is attached.

The augmented polymeric piercing member can be either one of two broad classes: a solid lancet; or a needle with at least one lumen. The piercing tip can be either one of three broad classes: a solid lancet tip; a hollow needle tip; or a frangibly sealed hollow needle tip. The angle of the tip can be either: flat; oblique; compound; or conical. The polymeric component is burnable. The stiffening member can be either a single material or a composite material. The stiffening member can be metal, either hardened or unhardened. The stiffening member can have fibers within it such as glass or carbon. These fibers can be aligned or randomly dispersed. The stiffening member can be another plastic material which is harder. The stiffening member can be one or several parts. The stiffening member can be within or attached to the polymeric component.

The supporting base structures are the same as have been previously described. The lancet versions of the augmented polymeric piercing members go with FIGS. 20 through 23. The hollow needle versions go with FIGS. 24 through 27.

The following will expand on the general ,description of the augmented polymeric piercing member. They are described in FIGS. 34 through 51. Although the designs are shown in the hollow needle versions, FIGS. 34 through 49 can also be produced as lancets.

FIG. 34 shows a polymeric film material (84) which is spirally wound with a hard film stiffening member (88). The hard film stiffening member can be a metal foil; a hard, fiber filled, as with glass, laminate; or a metalized layer on the polymeric film material. The two materials are bonded together and spirally wound. The winding increases the longitudinal strength of the piercing member. FIG. 34 can be used with any of the supporting base structures previously described.

FIGS. 35 through 37 are schematic representations of a single stiffening member (90) integrally engaged with a needle composed of a polymeric material (80). The stiffening member can preferably be co-extruded with the polymeric material. Although, in the case of FIGS. 36 and 37 it can be attached after extrusion. When the stiffening member is made from a ferrous based metal that responds to magnetism, then the augmented polymeric piercing member can be magnetically oriented during the tip sharpening process so that the stiffening member will be at the apex of the piercing tip, thereby facilitating the piercing process.

FIGS. 38 through 40 show several stiffening members (90) in different relationships with the polymeric component (80). The place of attachment is shown by junction (92).

FIGS. 41 through 43 show arcuate stiffening members. FIG. 49 is a longitudinal cross section of FIG. 41 which illustrates that the stiffening member (90) extends for the entire length of the augmented polymeric piercing member.

FIGS. 44 through 47 show triangular shaped stiffening members (90) in different relationships with the polymeric component (80).

FIG. 48 shows an arcuate stiffening member (90). The polymeric component (80) of both FIGS. 46 and 48 are films which are attached at junction (92).

FIGS. 50 and 51 show perspective views of a triangular shaped stiffening member (90) which has a polymeric component (80) in the form of a film attached. The stiffening member has a sharpened edge (94). In FIG. 50, an opening (96) is left at the tip. In FIG. 51, the tip is frangibly sealed by the polymeric component (80). In the previously described frangibly sealed tips, the seal would be pushed open by the exertion of pressure within the needle. In this frangibly sealed tip, the seal is broken during the piercing process by the skin forcing the polymeric component (80) against the sharpened edge (94), thereby cutting it and pushing the flap into the lumen, The flap doesn't come off, it stays attached to the rest of the polymeric component.

Frangibly sealed piercing tips make the augmented polymeric hypodermic devices illustrated by FIGS. 67 through 73 possible. An augmented polymeric piercing member with a frangibly sealed tip like that of FIG. 51 is shown with all of the devices. However, the other types of frangibly sealed tips which are shown in FIGS. 13 through 17 can also be used along with the various augmenting means that are applicable to these flexible needle designs.

FIG. 67 shows a one time use phlebotomy device. Unlike present blood withdrawal systems, this device can be operated with one hand. During the piercing process, the frangibly sealed tip (214) is broken. Vacuum (138) draws the blood into the vacuum container (134) where it comes in contact with test strip (136). The test strip (136 ) can be treated so that it will detect single or multiple medical conditions. After recording the data, the device can be destroyed.

FIG. 68 shows another one time use phlebotomy device. After the blood is withdrawn as before into the vacuum container (134), the reagent container (212) is rotated in the rotation ring (136) so that the reagent container opening (140) aligns with the vacuum container opening (138). The reagent (210) is then allowed to mix with the blood so that specific or multiple medical tests can be performed. FIG. 69 is a cross sectional view of FIG. 68 showing how the two opening are aligned.

FIG. 70 through 73 shows a one time use prefilled ampule for the low cost injection of medicaments. The ampule (142) is made by a vacuum forming process which leaves a void into which a medicament (144) is sealed at seam (146). After skin penetration, finger pressure is exerted on the ampule (142) expelling medicament (144) through the frangibly sealed tip into the patient. Before use, the device is stored in an aseptic container (148) as shown in FIG. 73. The ampule is kept from moving by receiving slots (150) in the side wall of the container. The end cap (154) which aseptically closes the container is shown in FIG. 71. The pull tab (156) is pulled to break the antiseptic wipe seal (158) so that the antiseptic wipe (152) can cleanse the injection area. Instructions can be printed on the container. The device lends itself to patient administered injection. It is ideal for primitive and remote locations. It is self-contained, inexpensive and easily destroyed after use.

Third, the intravenous catheter devices which employ a slidable piercing member which is either removably or retractably engaged with the polymeric cannula will be discussed. FIGS. 74 through 76 show an intravenous catheter device with a removably engaged piercing member. FIGS. 77 and 78 show an intravenous catheter device with a retractably engaged piercing member.

To use the intravenous catheter device of FIG. 74, first a tube or reservoir is attached to coupler (162). Then, the i.v. piercer (164) provided with an i.v. piercing tip (170) is inserted into the patient by pushing manually forward on the handle (160). Next, the wings (174), which are attached to the polymeric cannula (168), are bent upwards and pinched together along the fold lines (218). The notches (216) allow for easier bending of the wings. This motion separates the wings (174) with the attached polymeric cannula (168) from the i.v. piercer (164) and the handle (160) attached to it. While the wings are held steady, the handle with the attached i.v. piercer is manually withdrawn and discarded. The polymeric cannula is thus positioned alone in the vein. The wings are then secured to the patient with adhesive tape which goes over the wings (174) and between the tape guides (176). FIG. 75 is a cross sectional view of the piercing member which shows that the i.v. piercer (168) partially surrounds the polymeric cannula (168) in a frictional, yet slidable engagement. Blood can be viewed through the top of the clear polymeric cannula even while the i.v. piercer is temporarily engaged. FIG. 76 shows a side view of the device with the wings folded in the "up" position.

FIG. 78 shows another intravenous catheter device in which the piercing member is retractably located within the cannula. Zeus Industrial Products, Inc. of New Jersey makes a micro-diameter plastic tubing with multiple lumens which is ideal for this application. First, the device is attached to a tube or reservoir with coupler (162). After insertion into the vein of the patient, the i.v. piercing tip (170) is withdrawn into the polymeric cannula (168) by the button (192) being slid within the button groove (186) back to the retracted button position (190) past the button detent (188). Then, wing (174) with attached top seal (196) is folded along self-hinge (182) until the top seal (196) mates with the bottom seal (194). The button groove projection (184) mates with the button groove (186) while the button stop (198) locks the button (192) into the retracted position (190). The device is secured to the patient with adhesive tape which goes over the wings (174) and between the tape guides (176). FIG. 77 shows a cross sectional view of FIG. 78 in which the i.v. piercer (164) is located within the wall of the polymeric cannula (168). This type of device can also be made in which the i.v. piercer is located within the central lumen of the polymeric cannula.

These augmented polymeric hypodermic devices will make all hypodermic processes less painful and more safe. They will be cheaper to produce and easier to dispose. They will be a revolutionary change in a field that has not changed in over 100 years.

The foregoing description of the preferred embodiments of the invention has been presented for the purpose of illustration and description. It is not intended to be exhaustive or to limit the invention to the precise form disclosed. Many modifications and variations are possible in the light of the above teaching. It is intended that the scope of the invention be limited not by this detailed description, but rather by the claims appended hereto.

I claim:

1. A hypodermic device for performing a piercing process comprising:
   a non-slidable, integral combination including;
      a polymeric component and
      an augmenting means that extends longitudinally a substantial length of said polymeric component which stiffens said polymeric component;
   wherein said integral combination forms an augmented polymeric hypodermic device having at least one lumen, and a piercing tip with a frangible seal which is non-removable.

2. The hypodermic device of claim 1 wherein said augmenting means is spirally wound.

3. The hypodermic device of claim 1 wherein said augmenting mean comprises at least one stiffening member which is selected from the group consisting of arcuate shaped and "V" shaped.

4. The hypodermic device of claim 1 wherein said augmenting means comprises filler material dispersed within said polymeric component.

5. The hypodermic device of claim 1 wherein said frangible seal comprises at least one weakened area.

6. A hypodermic device for performing a piercing process comprising:
   a non-slidable, integral combination including;
      a polymeric component and
      an augmenting means that extends longitudinally a substantial length of said polymeric component which stiffens said polymeric component;

wherein said integral combination forms an augmented polymeric hypodermic device having at least one lumen, and a piercing tip with a frangible seal which is non-removable;

further comprising that said integral combination is communicably attached to a reservoir designed to receive bodily fluids withdrawn from a patient.

7. The hypodermic device of claim 6 wherein said augmenting means comprises at least one stiffening member which is selected from the group consisting of: arcuate shaped and "V" shaped.

8. The hypodermic device of claim 6 wherein said reservoir is a vacuum container.

9. The hypodermic device of claim 6 wherein said reservoir contains a medium designed to perform a medical test selected from the group consisting of: test strip and reagent.

10. The hypodermic device of claim 6 wherein said augmenting means comprises filler material dispersed within said polymeric component.

11. The hypodermic device of claim 6 wherein said frangible seal comprises at least one weakened area.

12. A hypodermic device for performing a piercing process comprising:

a non-slidable, integral combination including;
a polymeric component and
an augmenting means that extends longitudinally a substantial length of said polymeric component which stiffens said polymeric component;

wherein said integral combination forms an augmented polymeric hypodermic device having at least one lumen, and a piercing tip with a frangible seal which is non-removable;

further comprising that said integral combination is communicably attached to a reservoir designed to deliver generally fluid material to a patient.

13. The hypodermic device of claim 12 wherein said augmenting means comprises at least one stiffening member which is selected from the group consisting of: arcuate shaped and "V" shaped.

14. The hypodermic device of claim 12 wherein said reservoir is a prefilled ampule.

15. The hypodermic device of claim 12 wherein said augmenting means comprises filler material dispersed within said polymeric component.

16. The hypodermic device of claim 12 wherein said frangible seal comprises at least one weakened area.

17. A hypodermic device for performing a piercing process comprising:

a non-slidable, integral combination including;
a polymeric component and
an augmenting means that extends longitudinally a substantial length within said polymeric component which stiffens said polymeric component;

wherein said integral combination forms an augmented polymeric hypodermic device having at least one lumen, and a piercing tip with at least one integral frangible seal which is non-removable.

18. A hypodermic device for performing a piercing process comprising:

a non-slidable, integral combination including;
a polymeric component and
an augmenting means that extends longitudinally a substantial length attached to said polymeric component which stiffens said polymeric component;

wherein said integral combination forms an augmented polymeric hypodermic device having at least one lumen, and a piercing tip with at least one integral frangible seal which is non-removable.

* * * * *